United States Patent
Kaushik et al.

(10) Patent No.: US 10,794,978 B2
(45) Date of Patent: Oct. 6, 2020

(54) SYSTEM AND METHOD FOR CORRECTING ONE OR MORE ARTIFACTS WITHIN A MULTI-SPECTRAL MAGNETIC RESONANCE IMAGE

(71) Applicants: General Electric Company, Schenectady, NY (US); MEDICAL COLLEGE OF WISCONSIN, Milwaukee, WI (US)

(72) Inventors: Suryanarayanan Sivaran Kaushik, Waukesha, WI (US); Kevin Matthew Koch, Milwaukee, WI (US)

(73) Assignees: GENERAL ELECTRIC COMPANY, Schenectady, NY (US); THE MEDICAL COLLEGE OF WISCONSIN, Milwaukee, WI (US)

( * ) Notice: Subject to any disclaimer, the term of this patent is extended or adjusted under 35 U.S.C. 154(b) by 371 days.

(21) Appl. No.: 15/947,291

(22) Filed: Apr. 6, 2018

(65) Prior Publication Data

US 2018/0292496 A1 Oct. 11, 2018

Related U.S. Application Data

(60) Provisional application No. 62/482,913, filed on Apr. 7, 2017.

(51) Int. Cl.
*G01R 33/56* (2006.01)
*G01R 33/483* (2006.01)
(Continued)

(52) U.S. Cl.
CPC ........ *G01R 33/5608* (2013.01); *A61B 5/0035* (2013.01); *A61B 5/055* (2013.01); *G01R 33/4833* (2013.01); *G01R 33/56536* (2013.01)

(58) Field of Classification Search
CPC ........... G01R 33/5608; G01R 33/4833; G01R 33/243; G01R 33/443; G01R 33/5659;
(Continued)

(56) References Cited

U.S. PATENT DOCUMENTS

| | | | |
|---|---|---|---|
| 2017/0003370 A1* | 1/2017 | Chen | G01R 33/56536 |
| 2018/0267126 A1* | 9/2018 | Shi | G01R 33/5608 |

OTHER PUBLICATIONS

Koch et al.; Imaging Near Metal: The Impact of Extreme Static Local Field Gradients on Frequency Encoding Process; Magnetic Resonance in Medicine (2014).
(Continued)

*Primary Examiner* — Amy He
(74) *Attorney, Agent, or Firm* — Grogan, Tuccillo & Vanderleeden, LLP

(57) ABSTRACT

A method for correcting one or more artifacts within a multi-spectral magnetic resonance image is provided. The method includes acquiring a plurality of spectral bins each including a plurality of voxels and corresponding to a different frequency of MR signals emitted by an imaged object. The plurality of voxels of each spectral bin correspond to the frequency of the spectral bin so as to define a spatial coverage of the spectral bin. The method further includes expanding each spectral bin by increasing the spatial coverage of the spectral bin, and generating the multi-spectral magnetic resonance image based at least in part on the expanded spectral bins.

20 Claims, 12 Drawing Sheets

(51) Int. Cl.
*A61B 5/00* (2006.01)
*G01R 33/565* (2006.01)
*A61B 5/055* (2006.01)

(58) Field of Classification Search
CPC ........ G01R 33/56572; G01R 33/56536; A61B 5/0035; A61B 5/055; A61B 5/0037; G06T 5/002; G06T 5/20; G06T 7/0012
See application file for complete search history.

(56) References Cited

OTHER PUBLICATIONS

Koch et al.; Imaging Near Metal with a MAVRIC-SEMAC Hybrid; Magnetic Resonance in Medicine (2011).
Smith et al.; Characterizing the Limits of Magnetic Resonance Imaging Near Metallic Prostheses; Magn Reson Med. Dec. 2015.
Wenmiao, et al.; SEMAC: Slice Encoding for Metal Artifact Correction in MRI; Magn Reson Med (2009).

\* cited by examiner

SYSTEM AND METHOD FOR CORRECTING ONE OR MORE ARTIFACTS WITHIN A MULTI-SPECTRAL MAGNETIC RESONANCE IMAGE

CROSS-REFERENCE TO RELATED APPLICATIONS

This application claims priority to and the benefit of U.S. Provisional Pat. App. Ser. No. 62/482,913, filed Apr. 7, 2017, the disclosure of which is incorporated herein by reference in its entirety.

BACKGROUND

Technical Field

This disclosure relates to a system and method for correcting one or more artifacts within a multi-spectral magnetic resonance image.

Discussion of Art

MRI is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclei in the subject to be imaged. The nuclei are excited by a radio frequency ("RF") signal/pulse transmitted by a RF coil at characteristics NMR (Larmor) frequencies. By spatially disturbing localized magnetic fields surrounding the subject and analyzing the resulting RF responses, also referred to hereinafter as the "MR signal," from the nuclei as the excited protons relax back to their lower energy normal state, a map or image of these nuclei responses as a function of their spatial location is generated and displayed. An image of the nuclei responses, also referred to hereinafter as an "MRI image," provides a non-invasive view of a subject's internal structure.

Traditional MRI systems sometimes have difficulty imaging body tissues surrounding metal medical implants, e.g., stents, pins, screws, etc., also referred to hereinafter simply as "metal implants," due to electromagnetic interference resulting from the interaction of the metal implants with the MR signal and/or magnetic gradients applied to the patient/object being imaged. In particular, metal implants typically cause numerous artifacts to appear in the acquired images.

Accordingly, several three-dimensional ("3D") multi-spectral MRI sequences ("3D-MSI") such as MAVRIC SL and SEMAC have been developed to mitigate the effect of metal implants by overcoming the broadened frequency distribution around metal implants via combining several sub-images acquired at distinct frequency offsets from the Larmor frequency. While such 3D-MSI techniques have been successful at mitigating most types of artifacts in images for body tissues near metal implants, such techniques are often unable to correct artifacts known as "pile-ups," which are subtle fluctuations in the MR signal intensity that appear as ripples within an MR image typically caused by metal implants.

Thus, an improved system and method for correcting one or more artifacts within a multi-spectral magnetic resonance image is generally desired.

BRIEF DESCRIPTION

In an embodiment, a method of correcting one or more artifacts within a multi-spectral magnetic resonance image is provided. The method includes acquiring a plurality of spectral bins each including a plurality of voxels and corresponding to a different frequency of MR signals emitted by an imaged object. The plurality of voxels of each spectral bin correspond to the frequency of the spectral bin so as to define a spatial coverage of the spectral bin. The method further includes expanding each spectral bin by increasing the spatial coverage of the spectral bin, and generating the multi-spectral magnetic resonance image based at least in part on the expanded spectral bins.

In another embodiment, a system for correcting one or more artifacts within a multi-spectral magnetic resonance image is provided. The system includes an MRI controller in electronic communication with a magnet assembly and operative to acquire a plurality of spectral bins each including a plurality of voxels and corresponding to a different frequency of MR signals emitted by an imaged object. The plurality of voxels of each spectral bin corresponds to the frequency of the spectral bin so as to define a spatial coverage of the spectral bin. The MRI controller is further operative to expand each spectral bin, and to generate the multi-spectral magnetic resonance image based at least in part on the expanded spectral bins. Each spectral bin is expanded by increasing the spatial coverage of the spectral bin.

In yet another embodiment, a non-transitory computer readable medium storing instructions is provided. The stored instructions are configured to adapt an MRI controller to acquire a plurality of spectral bins each including a plurality of voxels and corresponding to a different frequency of MR signals emitted by an imaged object. The plurality of voxels of each spectral bin correspond to the frequency of the spectral bin so as to define a spatial coverage of the spectral bin. The stored instructions are further configured to adapt the MRI controller to expand each spectral bin, and to generate the multi-spectral magnetic resonance image based at least in part on the expanded spectral bins. Each spectral bin is expanded by increasing the spatial coverage of the spectral bin.

DRAWINGS

Various aspects of this disclosure may be better understood upon reading the following detailed description and upon reference to the drawings in which.

Figure 14:
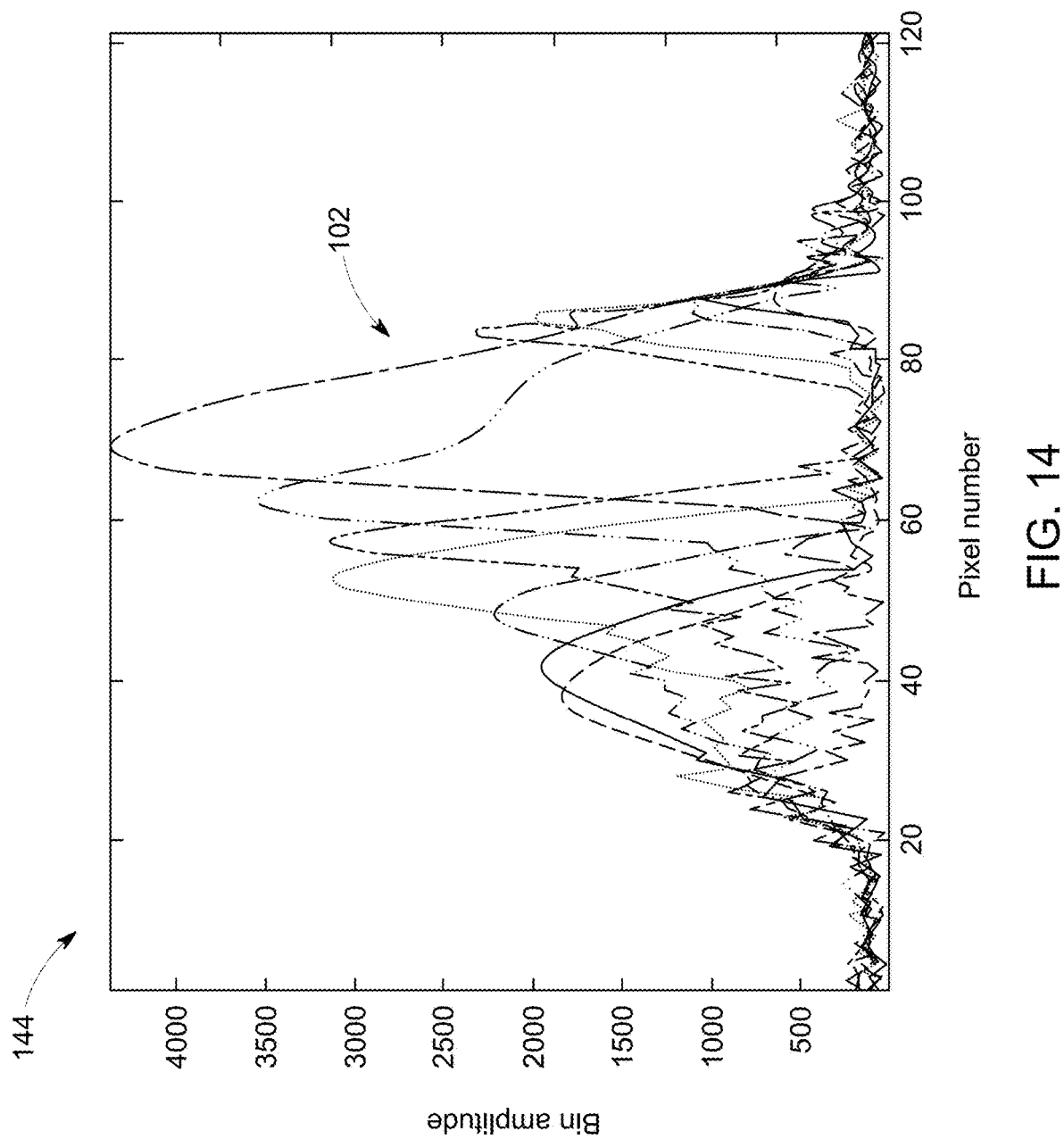
Figure 15:
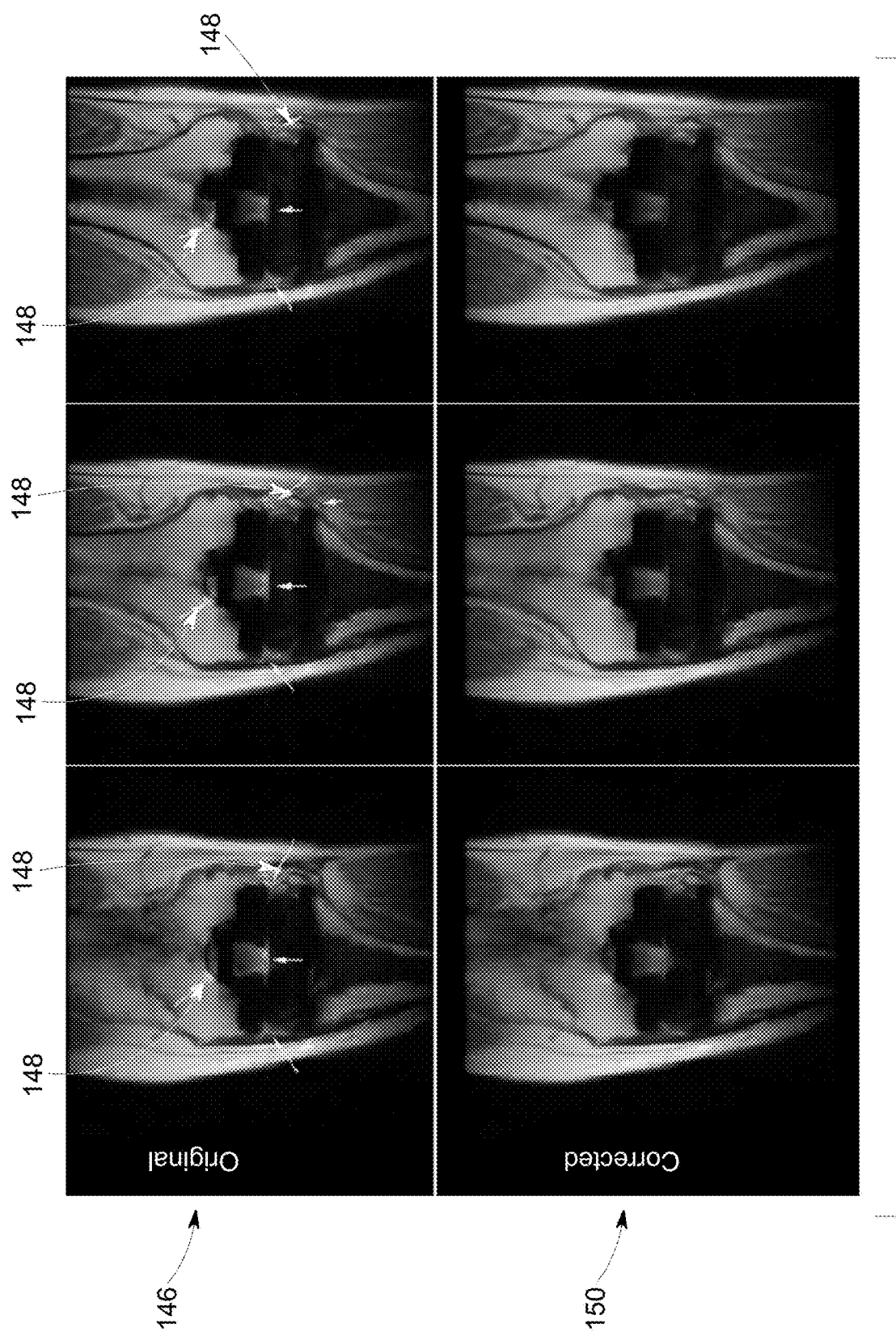

FIG. 14 is a diagram of a spectral profile of a multi-spectral MRI image generated from expanded spectral bins, in accordance with an exemplary embodiment of the present invention; and FIG. 15 is a diagram of a multi-spectral MRI image generated from unexpanded spectral bins and of a multi-spectral MRI image generated from expanded spectral bins, in accordance with an exemplary embodiment of the present invention.

The drawings illustrate specific aspects of the described systems and methods for monitoring a health status of a gradient coil. Together with the following description, the drawings demonstrate and explain the principles of the structures, methods, and principles described herein. In the drawings, the size of the components may be exaggerated or otherwise modified for clarity. Well-known structures, materials, or operations may not be shown or described in detail to avoid obscuring aspects of the described components, systems, and methods.

DETAILED DESCRIPTION

One or more specific embodiments of the present disclosure are described below in order to provide a thorough understanding. These described embodiments are only examples of systems and methods for correcting one or more artifacts within a multi-spectral magnetic resonance image. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

In addition, it should be understood that references to "one embodiment" or "an embodiment" of the present disclosure are not intended to be interpreted as excluding the existence of additional embodiments that also incorporate the recited features. Further, the limitations of the following claims are not written in means-plus-function format are not intended to be interpreted as such, unless and until such claim limitations expressly use the phrase "means for" followed by a statement of function void of further structure.

Further, while the embodiments disclosed herein are described with respect to an MRI system, it is to be understood that embodiments of the present invention may be applicable to other imaging systems in which pile-ups and/or other artifacts occur. Further still, as will be appreciated, embodiments of the present invention related imaging systems may be used to analyze tissue generally and are not limited to human tissue.

As stated above, pile-ups result from subtle fluctuations in the MR signal intensity in close proximity to metal implants. As will be understood, pile-ups typically result from non-ideal bin combinations, due to an incorrect bin separation and/or incorrectly applied pulses, within certain 3D MSI sequences that utilize Sinc pulses, e.g., SEMAC, with minimal overlap. As used herein, the terms "bin" and "spectral bin," refer to a grouping of voxels, and/or the associated sub-image, acquired at a particular frequency offset from the Larmor frequency in accordance with 3D-MSI. Pile-ups may also result from tissues located close to the surface of a metal implant that generate rapidly varying induction gradients that may exceed the frequency encoding gradient strength. As will be appreciated, the presence of such nonlinear local gradients may lead to the above-mentioned fluctuations in the intensity of the voxels and/or pixels of a combined image. The term "intensity," as used herein with respect to a voxel and/or pixel refers to the strength of the MR signal within the voxel and/or represented by the pixel.

Further, pile-ups may be more severe for higher susceptibility implants, e.g., implants made of stainless steel and/or Cobalt Chromium. As such, in certain aspects, the spectral bin intensities may show a subtle discontinuity in relation to neighboring bins, which may manifest as a ripple in the combined image when the bins are combined in a sum of squares fashion. Beyond the limits imposed by acquisition time, there are often minimal returns to image quality by increasing the spatial coverage beyond +/−12 kHz to sample the MR signal at higher frequencies. The term "spatial coverage," as used herein with respect to a bin, refers to the amount of the frequency spectrum of the MR signal represented by the voxels of a bin.

Thus, while it may be difficult and/or impossible to remove pile-ups during acquisition of the MR signal, embodiments of the present invention provide for a post-processing approach for mitigating and/or eliminating pile-ups. In particular, and as will be explained in greater detail below, embodiments of the invention disclosed herein take advantage of information extracted from a model of the spectral domain to accurately identify and/or correct local fluctuations in image intensity. In particular, in embodiments, voxels within the spectral bins corresponding to imaged regions within a patient/object located near a metal implant may be expanded/altered, e.g., blurred, via a filter, e.g., a moving average filter, so as to minimize discontinuities between outer boundaries of differing bins. As will be appreciated, when such expanded bins are combined in a sum of squares fashion, any pile-ups within the bins are significantly reduced and/or eliminated.

Figure 1:
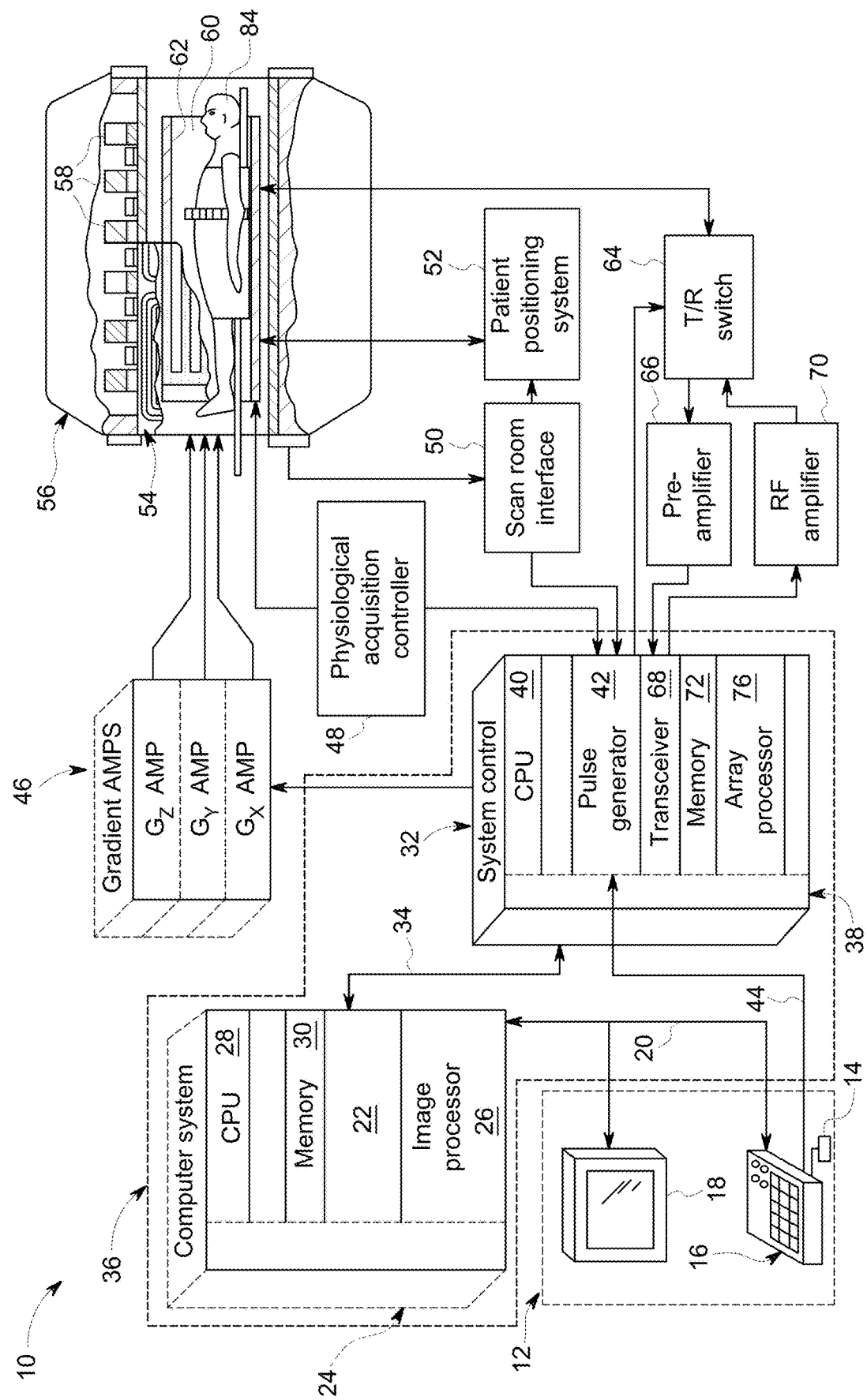
FIG. 1 is a block diagram of a system for correcting one or more artifacts within a multi-spectral magnetic resonance image, in accordance with an exemplary embodiment of the present invention.

Accordingly, now referring to FIG. 1, the major components of an MRI system 10 incorporating an embodiment of the invention are shown. Operation of the system 10 is controlled from the operator console 12, which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, which communicate with each other through a backplane 24. These include an image processor module 26, a CPU module 28 and a memory module 30, which may include a frame buffer for storing image data arrays. The computer system 22 communicates with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

The MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field $B_0$ throughout a target volume 60 that is enclosed by the magnet assembly 56) and a whole-body (transmit and receive) RF coil 62 (which, in operation, provides a transverse magnetic field $B_1$ that is generally perpendicular to $B_0$ throughout the target volume 60).

The resulting signals emitted by the excited nuclei in the patient may be sensed by the same RF coil 62 and coupled through the transmit/receive switch 64 to a preamplifier 66. The amplifier MR signals are demodulated, filtered, and digitized in the receiver section of a transceiver 68. The transmit/receive switch 64 is controlled by a signal from the pulse generator module 42 to electrically connect an RF amplifier 70 to the RF coil 62 during the transmit mode and to connect the preamplifier 66 to the RF coil 62 during the receive mode. The transmit/receive switch 64 can also enable a separate RF coil (for example, a surface coil) to be used in either transmit or receive mode.

The MR signals picked up by the RF coil 62 are digitized by the transceiver module 68 and transferred to a memory module 72 in the system control 32. A scan is complete when an array of raw k-space data has been acquired in the memory module 72. This raw k-space data/datum is rearranged into separate k-space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26 and conveyed to the operator console 12 and presented on the display 18.

Figure 2:
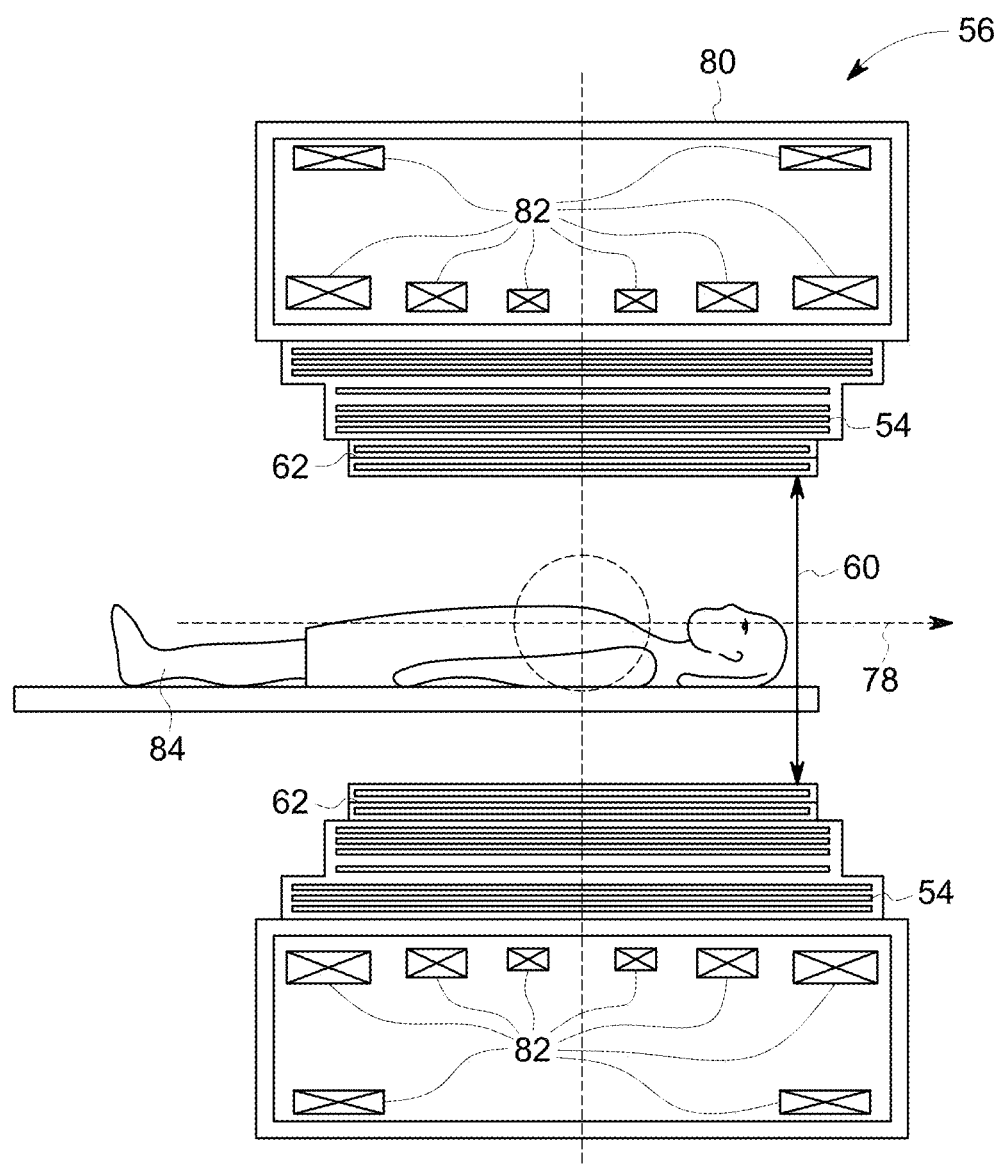
FIG. 2 is a schematic cross-sectional view of a magnet assembly of the system of FIG. 1, in accordance with an exemplary embodiment of the present invention.

As illustrated in FIG. 2, a schematic side elevation view of the magnet assembly 56 is shown in accordance with an embodiment of the invention. The magnet assembly 56 is cylindrical in shape having a center axis 78. The magnet assembly 56 includes a cryostat 80 and one or more radially aligned longitudinally spaced apart superconductive coils 82 that form the polarizing magnet 58. The superconductive coils 82 are capable of carrying large electrical currents and are designed to create the $B_0$ field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system 10 (FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MRI system may also utilize embodiments of the invention described below. As further shown in FIG. 2, a patient/imaged subject 84 is inserted into the magnet assembly 56.

Figure 3:
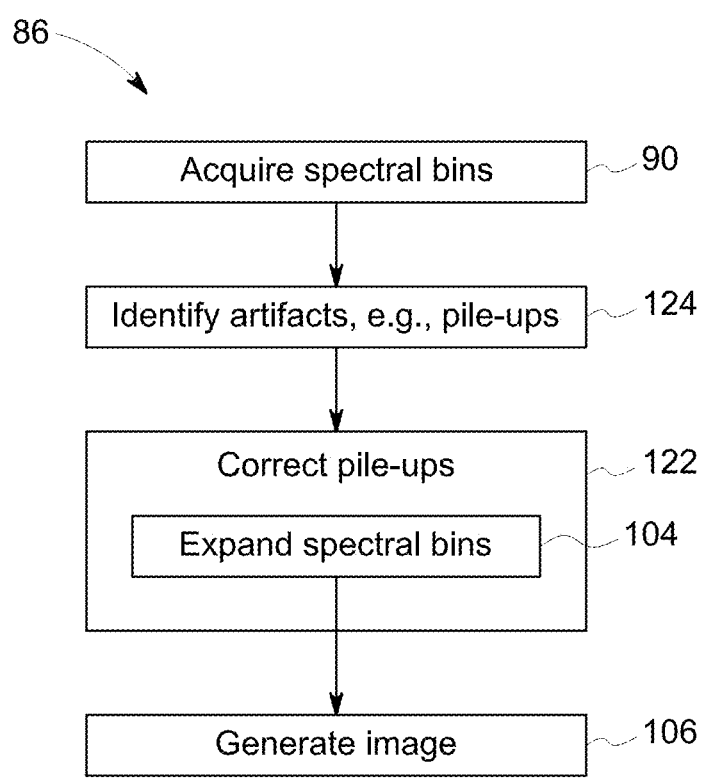
FIG. 3 is a flow chart depicting a method for correcting one or more artifacts within a multi-spectral magnetic resonance image utilizing the system of FIG. 1, in accordance with an exemplary embodiment of the present invention.
Figure 4:
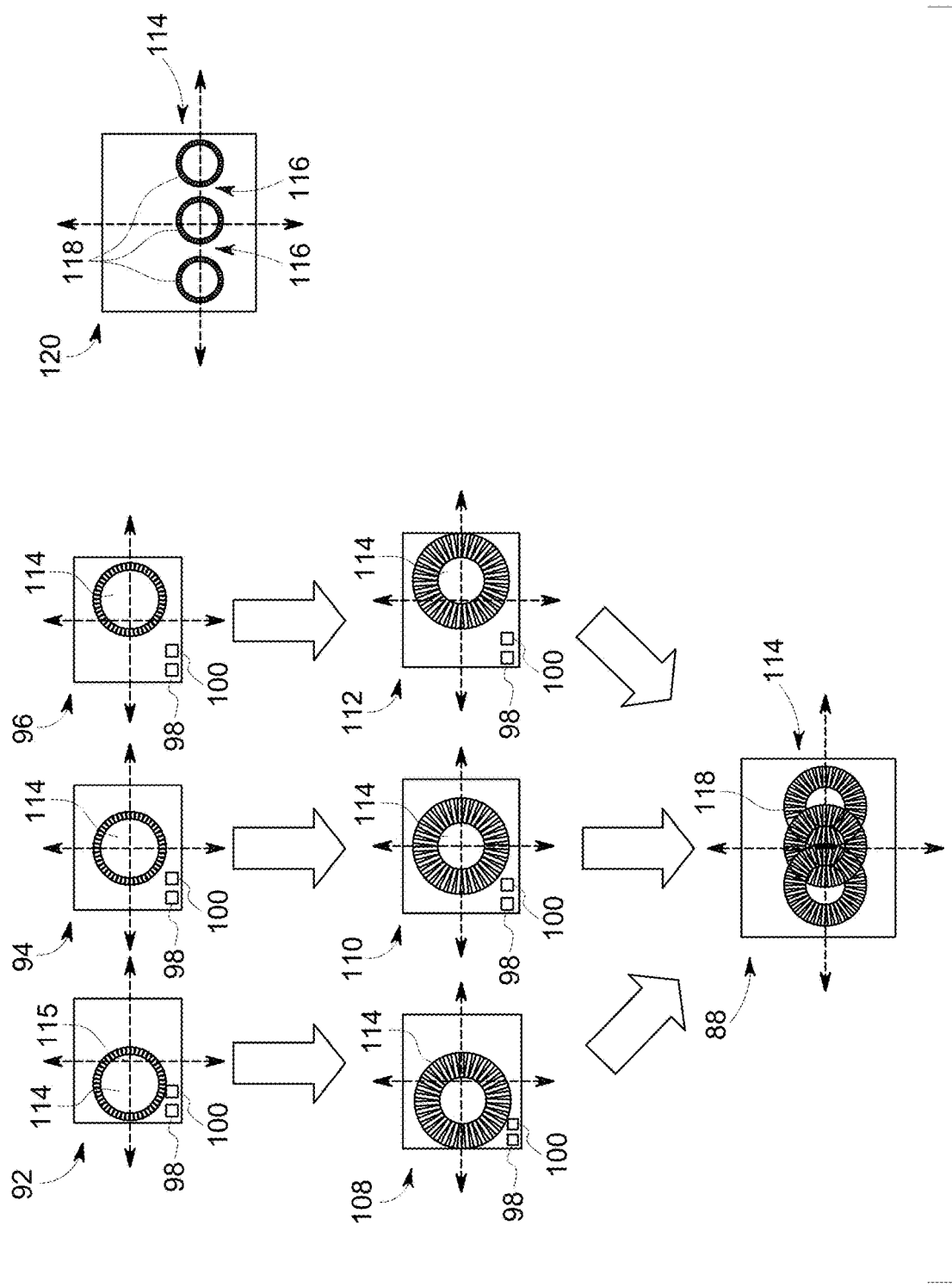
FIG. 4 is a diagram depicting the expansion of a plurality of spectral bins acquired via the system of FIG. 1, in accordance with an exemplary embodiment of the present invention.
Figure 13:
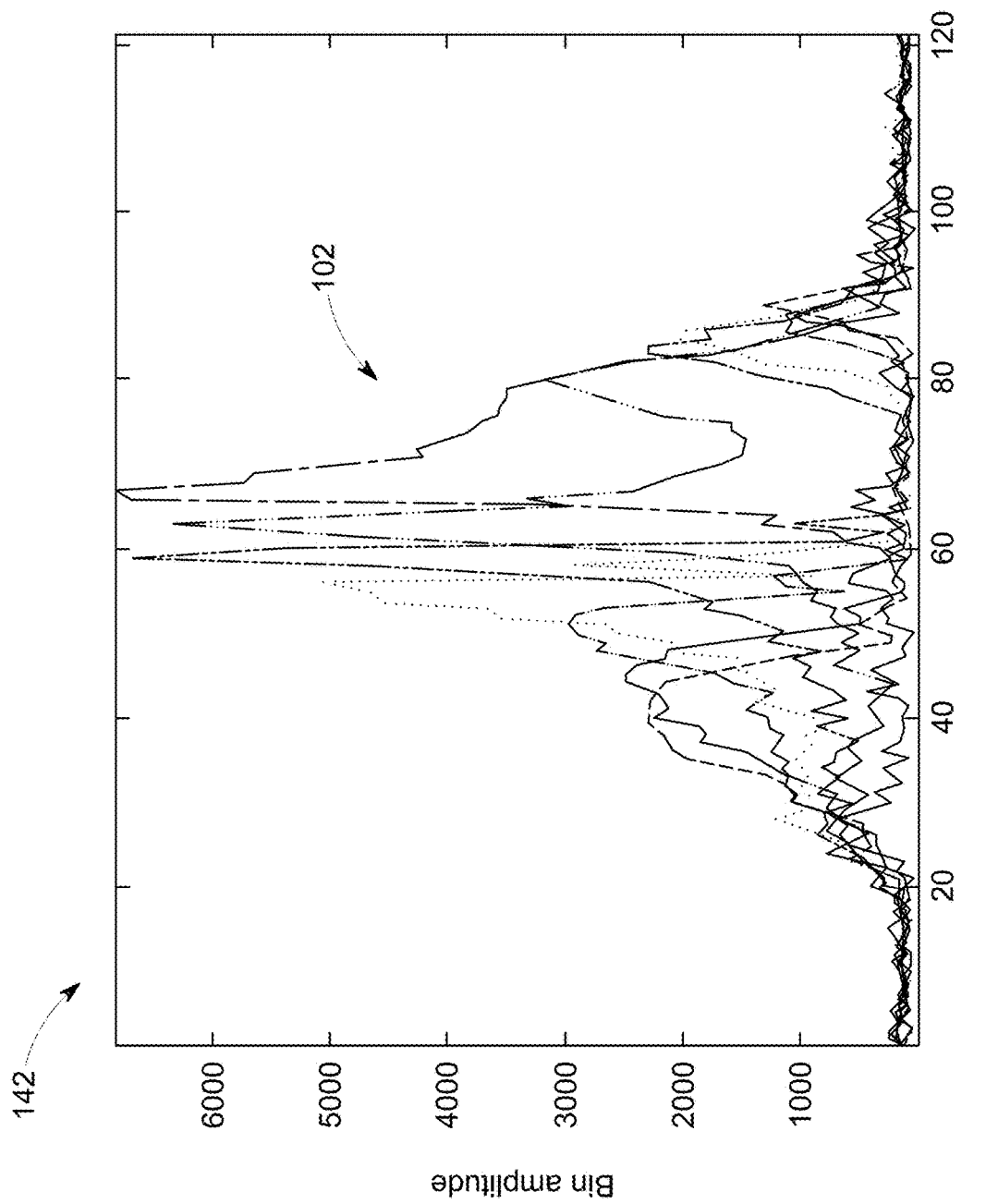
FIG. 13 is a diagram of a spectral profile of a multi-spectral MRI image generated from unexpanded spectral bins, in accordance with an exemplary embodiment of the present invention.

Turning now to FIGS. 3 and 4, a flow chart and accompanying diagram depicting an embodiment of the method 86 (FIG. 3) for correcting one or more artifacts, e.g., pile-ups, within a multi-spectral magnetic resonance image 88 (FIG. 4) utilizing the MRI system 10 (FIG. 1) are shown. The method includes acquiring, at step 90, a plurality of spectral bins 92, 94, 96 (FIG. 4) each including a plurality of voxels 98, 100 and corresponding to a different frequency of MR signals emitted by the imaged object/patient 84 (FIG. 2). As will be appreciated, the bins 92, 94, 96, may be acquired in accordance with 3D-MSI such that the pixels in the final image 88 have a bandwidth of about 1 kHz and provide a spectral coverage of about 24 kHz. The plurality of voxels 98, 100 of each spectral bin 92, 94, 96 correspond to the frequency of the spectral bin 92, 94, 96 so as to define a spatial coverage 102 (FIGS. 13 and 14) of the spectral bin 92, 94, 96. As further shown in FIG. 3, the method 86 also includes expanding, at step 104, each spectral bin 92, 94, 96 by increasing the spatial coverage 102 of the spectral bin 92, 94, 96, and generating, at step 106, the multi-spectral magnetic resonance image 88 based at least in part on the expanded spectral bins 108, 110, 112 (FIG. 4). As shown in FIG. 4, each bin 92, 94, 96 depicts a slightly different version of the same structure 114 within the patient 84, wherein the structure 114 in each unexpanded bin 92, 94, 96 is slightly shifted with respect to a common reference axis 115 such that combining the unexpanded bins 92, 94, 96 in a sum of squares fashion would result in gaps 116 between the boundaries 118 of the structure 114 in the summed non-corrected image 120, which in turn results in pile-ups. Expanding, at step 104, the spectral bins 92, 94, 96, however, results in overlapping of the boundaries 118 of the structure 114 when the expanded bins 108, 110, 112 are combined in a sum of squares fashion, which in turn reduces and/or eliminates pile-ups in the final corrected image 88.

As will be appreciated, in embodiments, expansion, at step 104, of the spectral bins 92, 94, 96 may form part of a more general process of correcting, at step 122, artifacts, and the method 86 may further include identifying, at step 124, artifacts, e.g., pile-ups, within the spectral bins 92, 94, 96, prior to correcting, at step 122, the artifacts.

Figure 5:
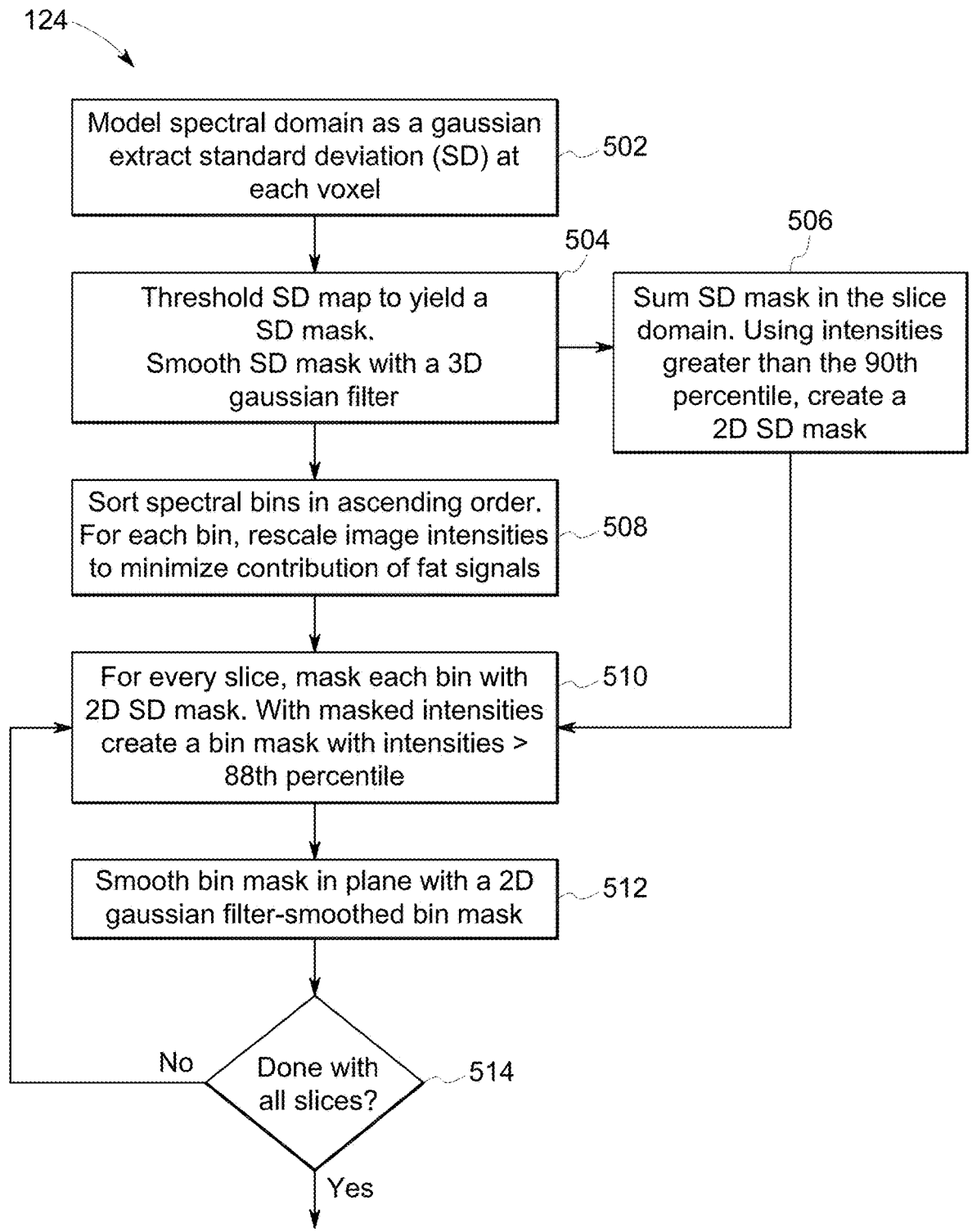
FIG. 5 is a flow chart depicting a process for identifying artifacts via the system of FIG. 1, in accordance with an exemplary embodiment of the present invention.
Figure 6:
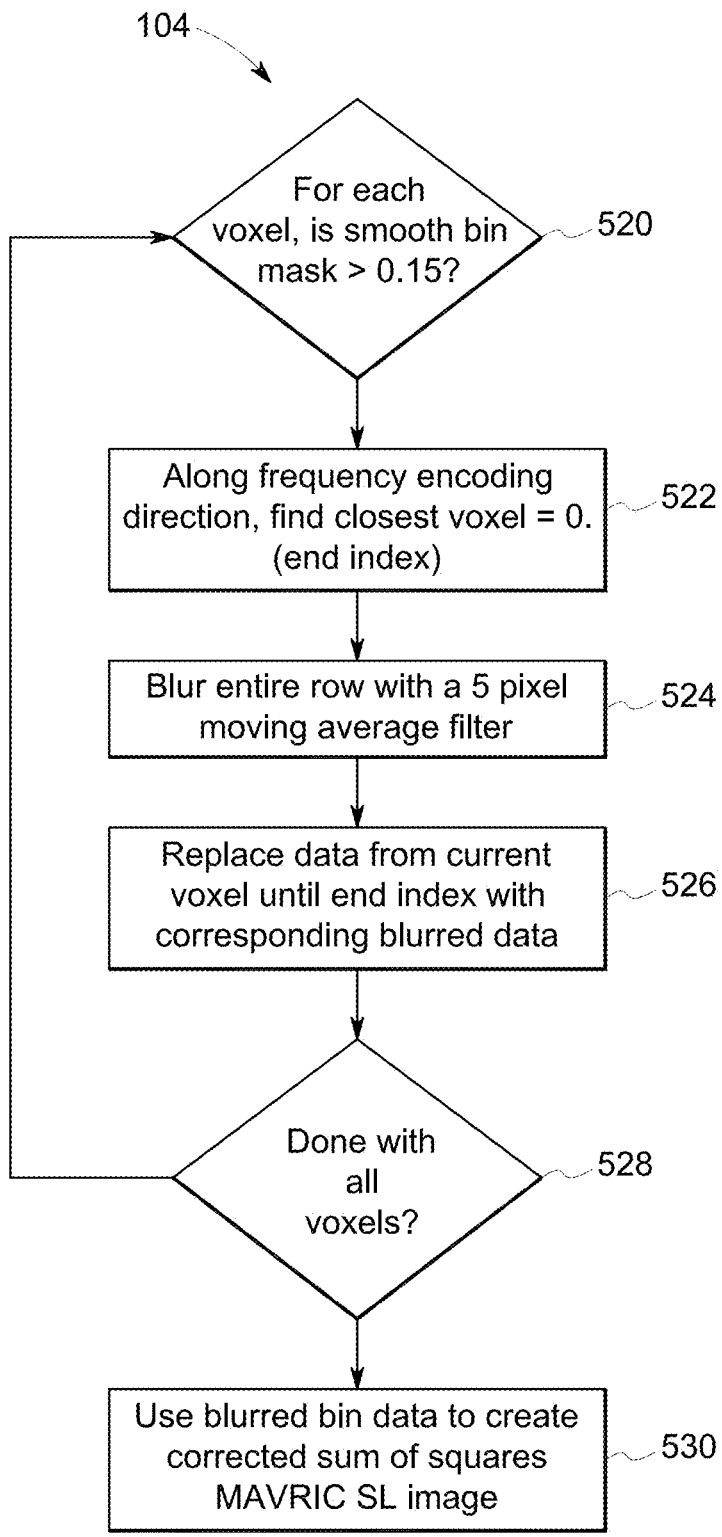
FIG. 6 is a flow chart depicting a process for expanding the plurality of spectral bins of FIG. 4, in accordance with an exemplary embodiment of the present invention.

Turning now to FIGS. 5 and 6, a flow chart depicting a process for identifying, at step 124, regions, i.e., one or more voxels 98, 100 (FIG. 4), of pile-ups within the bins 92, 94, 96 (FIG. 4) and for expanding, at step 104, the spectral bins 92, 94, 96 are shown. In embodiments, identifying, at step 124, regions may include modeling, at step 502, the spectral domain as a Gaussian Extract Standard deviation ("SD") at each voxel; thresholding, at step 504, the SD map to yield a SD mask, and smoothing the SD mask with a 3D Gaussian Filter. The SD mask may then be summed, at step 506, in the slice domain. In embodiments, identifying, at step 124, the regions may include sorting, at step 508, the spectral bins and scaling the image intensities. As shown by steps 510, 512, and 514, for each slice, each bin may be masked with the 2D SD mask so as to create/generate a bin mask with intensities greater than a pre-determined percentile, e.g., the eighty-eighty percentile.

Thus, as can be seen in FIG. 5, embodiments of the method 86 may utilize intensity based thresholding to identify, at step 124, regions of high intensity in the spectral bins 92, 94, 96, which in embodiments, may be acquired as part of a MAVRIC SL acquisition. Thus, in embodiments, the father away the corresponding frequency of a spectral bin 92, 94, 96 from the Larmor frequency, the larger the difference between the foreground and background MR signals, and therefore, the easier it is to identify regions within the spectral bin 92, 94, 96 that may produce pile-ups. Conversely, the closer the corresponding frequency of a spectral bin 92, 94, 96 to the Larmor frequency, the more difficult it becomes to identify regions that may contribute to pile-ups as the difference between the background noise and foreground of the MR signals shrinks. As will be appreciated, however, there are still identifiable signal intensities within the spectral bins 92, 94, 96 that can be utilized to determine regions within the spectral bins 92, 94, 96 that are likely to result in pile-up.

Accordingly, in embodiments, high MR signal intensities that arise due to j-coupling in body fat are first isolated and intensity corrected such that non-fat regions, and those that include fat, have the same mean intensity.

Figure 7:
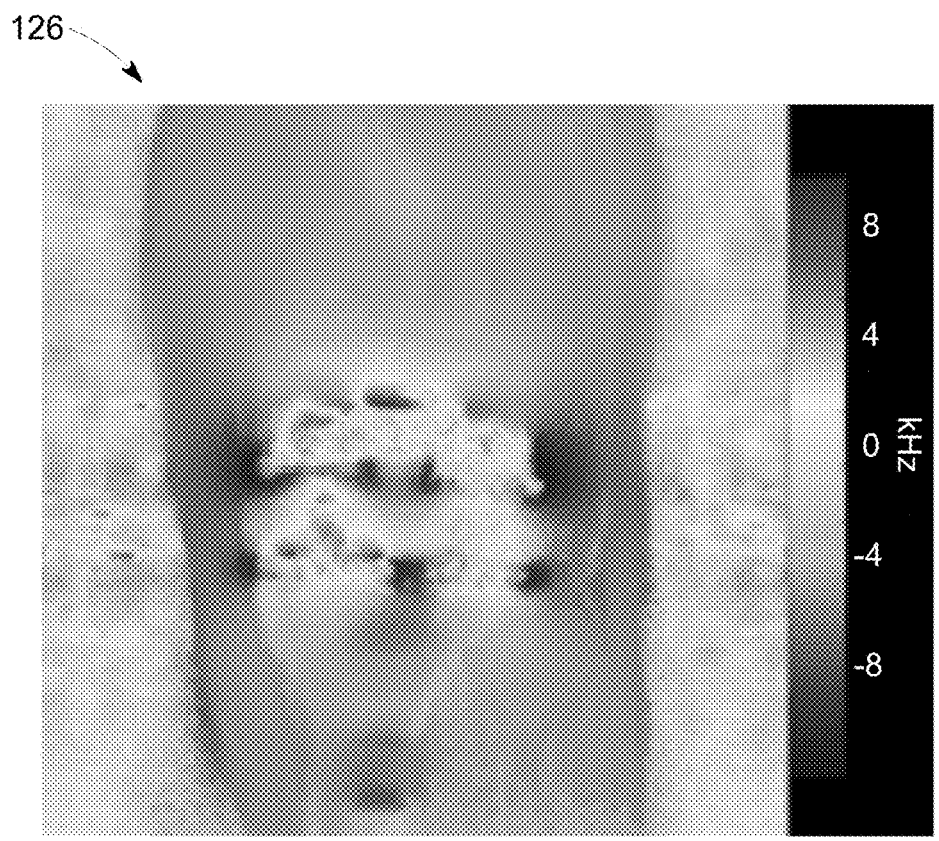
FIG. 7 is a diagram of a frequency map, in accordance with an exemplary embodiment of the present invention.
Figure 8:
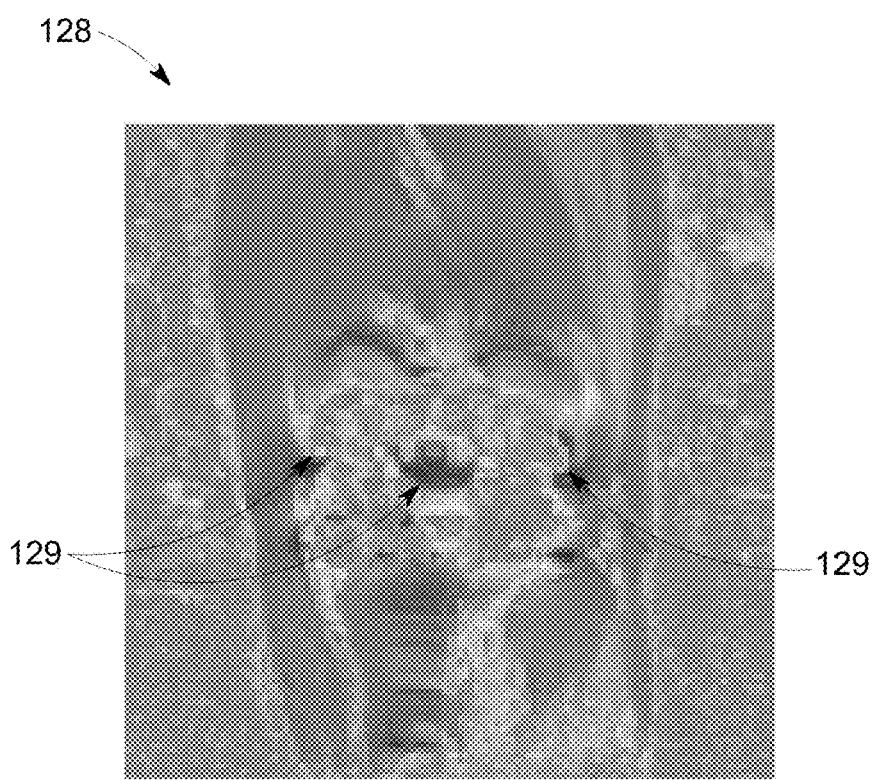
FIG. 8 is a diagram of a Gaussian standard deviation ("SD") map, in accordance with an exemplary embodiment of the present invention.
Figure 9:
FIG. 9 is a diagram of an SD mask, in accordance with an exemplary embodiment of the present invention.
Figure 10:
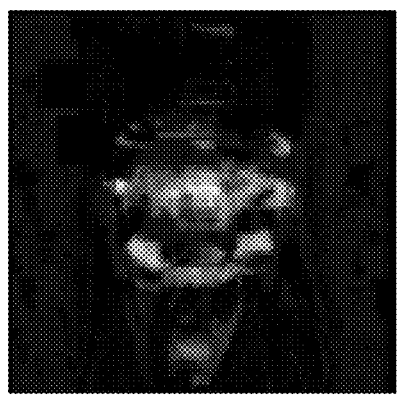
FIG. 10 is a diagram of a collapsed SD pile-up image, in accordance with an exemplary embodiment of the present invention.
Figure 11:
FIG. 11 is a diagram of a two-dimensional ("2D") SD mask, in accordance with an exemplary embodiment of the present invention.

Next, as shown by FIGS. 7-11, the spectral domain formed by the bins 92, 94, 96 may be modeled, at step 502 (FIG. 5), as a Gaussian to extract the standard deviation of the resulting Gaussian at every voxel 98, 100. As will be appreciated, FIG. 7 depicts a frequency map 126 of the uncorrected image 120 (FIG. 4), and FIG. 8 depicts an SD map 128 thereof. As shown in FIG. 8, regions 129 of the SD map 128 that have extensive pile-up undergo "bin compression" resulting in low SD values. As shown in FIG. 9, these regions may be thresholded, step 504 (FIG. 5), to yield an SD mask 130. The robustness of the SD mask 130 may be improved by summing, step 506 (FIG. 5), the SD mask 130 in the slice domain to yield a collapsed SD pile-up image 132 as shown in FIG. 10. The collapsed SD pile-up image 132 may in turn be thresholded to yield a 2D SD Mask 134, also referred to herein as a "standard-deviation-bin mask," as shown in FIG. 11. As will be understood, in embodiments, the 2D SD mask 134 helps to constrain regions in the spectral bins 92, 94, 96 which are likely to result in pile-ups, and may additionally improve segmentation of the spectral bins 92, 94, 96.

The spectral bins 92, 94, 96 may then be thresholded to pick the signal that will lead to pile-up in the uncorrected sum of squares image 120 (FIG. 4), i.e., a signal-intensity-bin mask may be applied to the bins 92, 94, 96. As will be appreciated, such thresholding may be performed on each slice-bin combination. Further, in embodiments, each 2D image may be multiplied by the 2D SD mask 134, and then thresholded to the masked signals that are greater than an empirical percentile, e.g., $88^{th}$, of the signal intensities. As shown in FIG. 5, the resulting bin mask may be smoothed in plane using a 2D Gaussian filter, resulting in the smoothed bin mask 136 shown in FIG. 12.

Referring back to FIG. 6, the spectral bins 92, 94, 96 (FIG. 4) may be expanded, at step 104, in accordance with the process shown. Accordingly, in embodiments, expanding 104 the spectral bins may include determining, at step 520, for each voxel, if the corresponding smooth bin mask is greater than a particular value, e.g., 0.15, and if true, finding, at step 522, the closet voxel that equals zero (0) along the frequency encoding direction; blurring, at step 524, the entire row with a moving average filter, e.g., a five (5) pixel moving average; and then replacing data, at step 526, from the current voxel. As represented by steps 528 and 530, after all voxels have been processed, the blurred bin data may be used to create a corrected sum of squares MAVRIC SL image.

Figure 12:
FIG. 12 is a diagram of a smoothed bin mask, in accordance with an exemplary embodiment of the present invention.

Thus, as will be appreciated, regions within the spectral bins 92, 94, 96 indicated by the smoothed bin mask 136 (FIG. 12) as potentially causing pile-ups may be subjected to a moving average filter, e.g., a 5-pixel average, in the frequency direction, so as to produce the expanded spectral bins 108, 110, 112 (FIG. 4). For example, as shown in FIG. 12, application of the moving average filter to the uncorrected/unexpended spectral bins, generally designated 138, results in the corrected/expanded bins, generally designated 140. The effects of the moving average filter can be better seen in FIGS. 13 and 14 which depict the spectral lines/line profiles 142 and 144 of the sums of square images of the uncorrected 138 and corrected 140 spectral bins shown in FIG. 12. Expansion, at step 104 (FIG. 3), of the spectral bins 138 via the moving average filter smooths the line profiles 144, and/or reduces discontinuities between neighboring spectral bins. Accordingly, FIG. 15 depicts the result of combining the expanded bins 140 in a sum of squares fashion to generate/produce a corrected 3D MSI image. As will be appreciated, the uncorrected images, generally designated 146, have regions associated with pile-ups marked by arrows 148, whereas the pile-ups in the corrected images 150 have been reduced and/or eliminated.

Further, in embodiments, expansion, at step 104 (FIG. 3), of the spectral bins 92, 94, 96 may be accomplished via morphological dilation of the gray scale for the bin intensities. Accordingly, such embodiments may determine the distance between the boundaries of the smooth bin mask 136 for a given slice, and adapt the size of the structuring element to dilate the appropriate regions. As will be appreciated, an additional intensity correction step may be required to homogenize the regions where the correction/expansion was applied.

Further still, in certain aspects, an additional Fourier based approach may also be used in which a one-dimensional ("1D") kernel rasters through the magnitude image looking for "beat frequencies" that are consistent with those of a pile-up. As will be appreciated, incorporating such a 1D kernel may further restrict/constrain the regions within each spectral bin 92, 95, 96 subject to expansion, at step 104 (FIG. 3).

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium, e.g., a medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

Accordingly, by expanding regions within one or more spectral bins indicated as contributing to pile-ups, some embodiments of the present invention may provide for the reduction and/or elimination of pile-up artifacts within multi-spectral MRI images. Further, by only expanding regions within the uncorrected spectral bins that have been identified by a mask, some embodiments provide for the ability to correct pile-ups without substantially altering the remaining regions of the spectral bins.

In addition to any previously indicated modification, numerous other variations and alternative arrangements may be devised by those skilled in the art without departing from the spirit and scope of this invention, and the appended claims are intended to cover such modifications and arrangements. Thus, while the invention has been described above with particularity and detail in connection with what is presently deemed to be the most practical and preferred aspects, it will be apparent to those of ordinary skill in the art that numerous modifications, including, but not limited to, form, function, manner of operations, and/or use may be made without departing from the principles and concepts set forth herein.

Finally, the examples and embodiments used herein are meant to be illustrative only and should not be construed to be limiting in any manner.

What is claimed is:

1. A method for correcting one or more artifacts within a multi-spectral magnetic resonance image comprising:
    acquiring a plurality of spectral bins each including a plurality of voxels and corresponding to a different frequency of MR signals emitted by an imaged object, the plurality of voxels of each spectral bin corresponding to the frequency of the spectral bin so as to define a spatial coverage of the spectral bin;
    expanding each spectral bin by increasing the spatial coverage of the spectral bin; and
    generating the multi-spectral magnetic resonance image based at least in part on the expanded spectral bins.

2. The method of claim 1, wherein generating the multi-spectral magnetic resonance image based at least in part on the expanded spectral bins comprises:
    summing the squares of each spatial coverage for each of the spectral bins.

3. The method of claim 1, wherein expanding each spectral bin by increasing the spatial coverage of the spectral bin comprises:
    applying a filter to one or more voxels of the plurality of each spectral bin.

4. The method of claim 3, wherein the filter is based at least in part on a moving average.

5. The method of claim 3, wherein the filter is applied to the one or more voxels along a direction corresponding to a frequency encoding direction of the multi-spectral magnetic resonance image.

6. The method of claim 3, wherein the filter is applied to the one or more voxels based at least in part on a mask that identifies the one or more voxels as contributing to the one or more artifacts.

7. The method of claim 6, wherein the mask is based at least in part on a standard-deviation-bin mask and a signal-intensity-bin mask.

8. The method of claim 1, wherein expanding each spectral bin by increasing the spatial coverage of the spectral bin comprises:
    morphologically dilating the spatial coverage of each spectral bin.

9. The method of claim 1, wherein at least one of the one or more artifacts is a pile-up.

10. A system for correcting one or more artifacts within a multi-spectral magnetic resonance image comprising:
  an MRI controller in electronic communication with a magnet assembly and operative to:
  acquire a plurality of spectral bins each including a plurality of voxels and corresponding to a different frequency of MR signals emitted by an imaged object, the plurality of voxels of each spectral bin corresponding to the frequency of the spectral bin so as to define a spatial coverage of the spectral bin;
  expand each spectral bin;
  generate the multi-spectral magnetic resonance image based at least in part on the expanded spectral bins; and
  wherein each spectral bin is expanded by increasing the spatial coverage of the spectral bin.

11. The system of claim 10, wherein the MRI controller generates the multi-spectral magnetic resonance image based at least in part on summing the squares of each spatial coverage for each of the spectral bins.

12. The system of claim 10, wherein the MRI controller increases the spatial coverage of the spectral bin by applying a filter to one or more voxels of the plurality of the spectral bin.

13. The system of claim 12, wherein the filter is based at least in part on a moving average.

14. The system of claim 12, wherein the filter is applied to the one or more voxels along a direction corresponding to a frequency encoding direction of the multi-spectral magnetic resonance image.

15. The system of claim 12, wherein the filter is applied to the one or more voxels based at least in part on a mask that identifies the one or more voxels as contributing to the one or more artifacts.

16. The system of claim 15, wherein the mask is based at least in part on a standard-deviation-bin mask and a signal-intensity-bin mask.

17. The system of claim 10, wherein the MRI controller increases the spatial coverage of the spectral bin by morphologically dilating the spatial coverage of the spectral bin.

18. The system of claim 10, wherein at least one of the one or more artifacts is a pile-up.

19. A non-transitory computer readable medium storing instructions configured to adapt an MRI controller to:
  acquire a plurality of spectral bins each including a plurality of voxels and corresponding to a different frequency of MR signals emitted by an imaged object, the plurality of voxels of each spectral bin corresponding to the frequency of the spectral bin so as to define a spatial coverage of the spectral bin;
  expand each spectral bin;
  generate the multi-spectral magnetic resonance image based at least in part on the expanded spectral bins; and
  wherein each spectral bin is expanded by increasing the spatial coverage of the spectral bin.

20. The non-transitory computer readable medium of claim 19, wherein the MRI controller generates the multi-spectral magnetic resonance image based at least in part on summing the squares of each spatial coverage for each of the spectral bins.

* * * * *